United States Patent [19]

Ueng et al.

[11] Patent Number: 4,620,010

[45] Date of Patent: Oct. 28, 1986

[54] PROCESS FOR PREPARING CARBOALKOXY SUBSTITUTED BENZOXAZOLE COMPOUNDS

[75] Inventors: Shou-Nan Ueng, West Haverstraw; Frederick A. Golec, Jr., Ossining, both of N.Y.

[73] Assignee: USV Pharmaceutical Corp., Tuckahoe, N.Y.

[21] Appl. No.: 594,644

[22] Filed: Mar. 29, 1984

[51] Int. Cl.$^4$ .................. C07D 263/58; C07D 263/60
[52] U.S. Cl. .................................. 548/217; 544/105; 544/102
[58] Field of Search .......................................... 548/217

[56] References Cited

U.S. PATENT DOCUMENTS

| | | | |
|---|---|---|---|
| 3,895,022 | 7/1975 | Moller et al. | 548/217 |
| 4,269,846 | 5/1981 | Huang et al. | 424/272 |
| 4,298,742 | 11/1981 | Brown et al. | 548/217 |
| 4,368,201 | 1/1983 | Huang et al. | 548/217 |

FOREIGN PATENT DOCUMENTS 90360 10/1983 European Pat. Off. .......... 548/217

1008267 10/1965 United Kingdom ................ 548/217

OTHER PUBLICATIONS

Dickoré, K. et al., Liebigs Ann. Chem., 733, 70-87, (1970).
Gaub, von Walter, et al., Liebigs Ann. Chem., 733, 59-69, (1970).
Llinares, J. et al., Can. J. Chem., 57, (8), 937-945, (1979).
Gilchrist, T. L. et al., J.A.C.S. Chem. Comm. 24, 962-963 (1975).
Moller, von Hinrich, Liebigs Ann. Chemie, 749, 1-11, (1970).
Saito, N., et al., Chem. Abstracts 50:13873h.
Tanaka, C. et al., Chem. Abstracts 60:16222d.
Tanaka, C. et al., Chem. Abstracts 58:3407d.

*Primary Examiner*—George F. Lesmes
*Assistant Examiner*—S. A. Gibson

[57] ABSTRACT

A process is provided to a unique preparation of carboalkoxy substituted or unsubstituted benzoxazole compounds from an amino-phenol compound.

7 Claims, No Drawings

PROCESS FOR PREPARING CARBOALKOXY SUBSTITUTED BENZOXAZOLE COMPOUNDS

FIELD OF THE INVENTION

The present invention relates to a unique preparation of carboalkoxy substituted or unsubstituted benzoxazole compounds from an amino-phenol compound. The compounds produced by the process of this invention are useful as anti-allergy agents.

DESCRIPTION OF THE PRIOR ART

There are several references in the prior art which describe the synthesis of oxazolecarboxylic acid derivatives. These include Saito, et al. in *J. Pharm. Soc. Japan*, 76, 305–7 (1956) (*Chem. Abstracts*, 50 13873h) describing the preparation of ethyl 5-phenyl 2-oxazolecarboxylate, 4-methyl 2-phenyl-5-oxazolecarboxylic acid, and the like.

Tanaka in *Yakugaku Zasshi*, 85(3), 186–93 (1965) Japan (Chem. Abstracts 62, 16222d) and Tauka, et al. in *Yakugaku Zasshi*, 82, 136–9 (1962) (Chem. Abstracts 58, 3407d) both describe the synthesis of similar oxazolecarboxylic acid derivatives but none of these references describe the production of carboalkoxy substituted benzoxazole, the compounds of the present invention.

Dickore, et al. in *Liebigs Ann. Chem.*, 733, 70–87 (1970) describe the snythesis of similar benzoxazoles but none of those compounds is the same as described in the present invention. Furthermore, the process of preparation of similar intermediates is different from the process in this invention. This article discloses 6-chloro-2H-1,4-benzoxazine-2,3-(4H)-dione to prepare a similar intermediate 3,6-Dichloro-2H-1,4-benzoxazine-2-one; however, this process is completely different from the process described in the present invention.

SUMMARY OF THE INVENTION

The present invention is directed to a process for the preparation of a carboalkoxy substituted or unsubstituted benzoxazole compound by reacting an amino-phenol compound having the formula I:

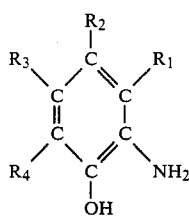

with an alkyl oxalyl chloride compound having the formula II

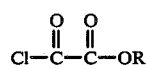

to form an oxamide ester having the formula III or III.HCl salt

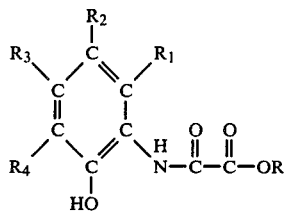

cyclochlorinating the oxamide ester III with chlorinating agents to form an imidoyl chloride compound having the formula IV

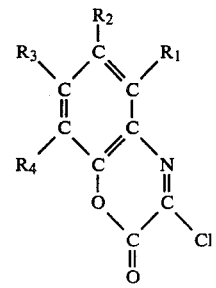

reacting the imidoyl chloride IV with metal alkoxide to form a benzoxazole product having the formula V

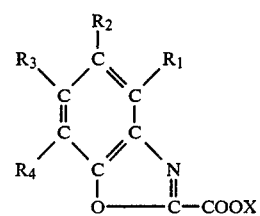

wherein
R is a $C_1$–$C_6$ alkyl group with a straight or branched chain;
X is selected from the group consisting of metal, hydrogen, an alkyl group containing 1 to 6 carbon atoms and an alkoxy alkyl group containing 1 to 6 carbon atoms
each $R_1$, $R_2$, $R_3$ and $R_4$ is independently hydrogen, cyano, aryl, cycloalkyl containing 3 to 5 carbon atoms, alkyl containing 1 to 5 carbon atoms, or may with an adjacent R substitution form an alkene bridge having 3 or 4 carbon atoms, with the proviso that when there is an alkene bridge the remaining R substitutions are independently hydrogen, cyano, cycloalkyl or alkyl.

DETAILED DESCRIPTION OF THE INVENTION

The present invention involves the reaction of a benzoxazole compound of formula I above with an alkyl oxalyl chloride compound of formula II above in solvents or without solvents at temperatures from about 0° C. to about 150° C., preferably about 10° C. to about 120° C., to produce an oxamide ester of the formula III or III . HCl salt above. The oxamide ester compound of the formula III is reacted with phosphorus oxychloride in solvents or without solvents at temperatures from about 0° C. to about 150° C., preferably about 10° C. to about 120° C., to product an imidoyl chloride of formula IV above.

The imidoyl chloride compound of formula IV is reacted with metal alkoxide at temperatures from about 0° C. to about 150° C., preferably about 70° C. to about 115° C., to produce the carboalkoxy substituted or unsubstituted benzoxazole compound V. These compounds have been found to be effective anti-allergy agents in their use in acceptable pharmaceutical compositions.

The amino phenol compounds of formula I above, used as starting materials in the process of this invention, can be any unsubstituted or halogen and/or alkyl substituted amino phenol compound. Typical of thse amino phenol compounds include, among others:
2-Amino-4-chlorophenol;
2-Amino-3-chlorophenol;
2-Amino-4-chloro-5-nitrophenol;
2-Amino-5-methylphenol;
2-Amino-5-t-butylphenol;
2-Amino-4,6-dimethylphenol;
1-Amino-5,6,7,8-tetrahydro-2-naphthalenol;
2-Amino-5,6,7,8-tetrahydro-2-naphthalenol;
2-Amino-4-nitro-6-chlorophenol;
2-Amino-3,5-dichlorophenol; and
3-Amino-5,6,7,8-tetrahydro-2-naphthalenol. The preferred compounds are 2-Amino-4-chlorophenol and 3-Amino-5,6,7,8-tetrahydro-2-naphthalenol.

The compounds of formula II above can be any alkyloxalyl chloride compound which includes methyl oxalyl chloride; ethyloxalyl chloride; propyloxalyl chloride; butyloxalyl chloride; hexyloxalyl chloride; and the like.

The resulting oxamide ester as described by formula III can be cyclochlorinated in the presence of agents such as phosphorus oxychloride, phosphorus trichloride, phosphorus pentoxide, polyphosphoric acid, thionyl chloride, and the like. The preferred agent is phosphorus oxychloride.

The resulting cyclochlorinated products of formula III are those compounds of formula IV. The compounds include:
3,6-Dichloro-2H-1,4-benzoxazin-2-one;
3,5-Dichloro-2H-1,4-benzoxazin-2-one;
3,6-Dichloro-7-nitro-2H-1,4-benzoxazin-2-one;
3,5,7-Trichloro-2H-1,4-benzoxazin-2-one;
3-Chloro-6,7,8,9-tetrahydronaph[2,3-d]-1,4-oxazine-2-one;
3,8-Dichloro-6-nitro-2H-1,4-benzoxazin-2-one;
3-Chloro-6-methyl-2H-1,4-benzoxazin-2-one;
3-Chloro-6-phenylmethyl-2H-1,4-benzoxazin-2-one;
3-Chloro-6-t-butyl-2H-1,4-benzoxazin-2-one;
3-Chloro-6,8-dimethyl-2H-1,4-benzoxazin-2-one;
3-Chloro-5,6,7,8-tetrahydronaph[3,4-c]-1,4-oxazine-2-one; and
3-Chloro-7,8,9,10-tetrahydronaph[1,2-c]-1,4-oxazine-2-one.

Solvents employed in the present invention may be any of those commonly used in organic preparations such as acetonitrile, methylene chloride, pyridine, dioxane, tetrahydrofuran, and similar solvents. Solvents are not always necessary since the reactants can be mixed to form the desired compounds at the reaction temperatures.

Compounds of formula IV may also prepared without isolation of foregoing oxamide ester of formula III or III . HCl salt.

Compounds having the formula IV are reacted with metal alkoxide to form a benzoxazole product having the formula V which are effective anti-allergy agents as determined by testing in procedures recognized to be cognent in vitro and in vivo models.

The compounds include:
Methyl 5-chloro-2-benzoxazole carboxylate;
Ethyl 5-chloro-2-benzoxazole carboxylate;
Sodium 5-chloro-2-benzoxazole carboxylate;
Methyl 4-chloro-2-benzoxazole carboxylate;
Methyl 5-chloro-6-nitro-2-benzoxazole carboxylate;
Methyl 4,6-dichloro-2-benzoxazole carboxylate;
Methyl 5-nitro-7-chloro-2-benzoxazole carboxylate;
Sodium 5,6,7,8-tetrahydronaphth[2,3-d]oxazole-2-carboxylate;
Methyl 5,6,7,8-tetrahydronaphth[2,3-d]oxazole-2-carboxylate;
Ethyl 5,6,7,8-tetrahydronaphth[2,3-d]oxazole-2-carboxylate;
Methyl 5,6,7,8-tetrahydronaphtha[1,2-c]oxazole-2-carboxylate;
and Methyl 5,6,7,8-tetrahydronaphtha[3,4-c]oxazole-2-carboxylate.

The preferred compounds are 2-Ethoxyethyl 5-chloro-2-benzoxazolecarboxylate and Methyl 5,6,7,8-tetrahydronaphth[2,3-d]oxazole-2-carboxylate.

The invention will be more fully illustrated in the examples which follow.

EXAMPLE 1

To a solution of 2-amino-4-chlorophenol (143.5 g, 1 mol) and triethylamine (111 g, 1.1 mol) in acetonitrile (800 ml) at 5° C. is added methyl oxalyl chloride over 1 hour below 8° C. The resulting mixture is then maintained at room temperature for several hours. The solid product is filtered, washed with methylene chloride to give 197 g (86% yield) of Methyl-N-(5-chloro-2-hydroxyphenyl)-oxamide.

EXAMPLE 2

To a suspension of 2-amino-4-chlorophenol (143.5 g, 1 mol) in acetonitrile (800 ml) at 5° C. is added methyl oxalyl chloride (134.5 g, 1.1 mol) below 8° C. The resulting mixture is then maintained at room temperature for several hours. The solid product is filtered, washed with methylene chloride to give 200 g (85% yield) of Methyl-N-(5-chloro-2-hydroxyphenyl)oxamide hydrochloride; m.p. 302°–303° C.

EXAMPLE 3

In a 500 ml flask is charge.d acetonitrile (200 ml) 5,6,7,8-tetrahydro-2-naphthalenol-methyl-3-N-oxamide (25 g, 0.1 mol) and phosphorus oxychloride (28 ml). The mixture was refluxed for 3 hours. After removal of solvent and excess of phosphorus oxychloride, the residue is then recrystallized from the mixture of toluene and methylcyclohexane (1:7) to give 18 g (80%) of 3-chloro-6,7,8,9-tetrahydronaph[2,3-d]-1,4-oxazine-2-one.

EXAMPLE 4

To a 500 ml flask is charged acetonitrile (200 ml) and 2-Amino-5,6,7,8-tetrahydro-2-naphthalenol (16.3 g) and cooled to 5° C. Methyl oxalyl chloride (10.11 ml) in acetonitrile (20 ml) is charged to the above mixture at 5° C. over 10 minutes and the mixture is then stirred at room temperature for 1 hour. Phosphorus oxychloride (28 ml) is added to the mixture and refluxed for three hours. After removal of solvent and excess of phosphorus oxychloride, the residue is then recrystallized from the mixture of toluene and methylcyclohexane to give 18 g (79%) of 3-Chloro-6,7,8,9-tetrahydro[2,3-d]-1,4-oxazine-2-one.

EXAMPLE 5

In a 500 ml flask is charged methanol.(100 ml), 3-chloro-6,7,8,9-tetrahydronaph[2,3-d]-1,4-oxazine-2-one (10 g) and sodium methoxide (5 g). The mixture is refluxed for 3 hours, then evaporated to dryness. The residue is charged with 200 ml of methylene chloride filtered. The resulting organic solution is evaporated and recrystallized from heptane to give 6 g (63% yield) of methyl-5,6,7,8-tetrahydronaph[2,3-d]oxazole-2-carboxylate with m.p. 120°–122° C.

What is claimed is:

1. A process for preparing a carboalkoxy substituted or unsubstituted benzoxazole compound which comprises reacting an aminophenol compound having the formula I

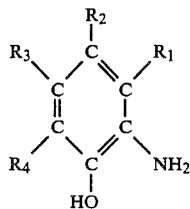

with an alkyl oxalyl chloride compound having the formula II

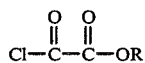

to form an oxamide ester having the formula III

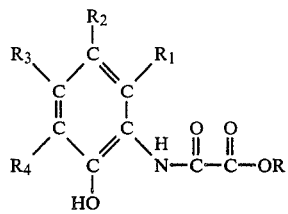

cyclochlorinating the oxamide ester III with phosphorus oxychloride to form an imidoyl chloride compound having the formula IV

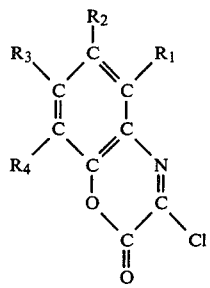

reacting the imidoyl chloride IV with alkali metal alkoxide the presence of an alcohol to form a benzoxazole product having the formula V

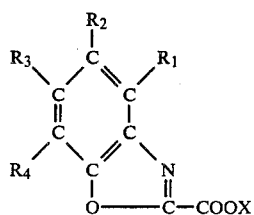

wherein
R is a $C_1$–$C_6$ alkyl group with a straight or branched chain;
X is selected from the group consisting of an alkyl group of 1 to 6 carbon atoms and an alkoxy alkyl group of 1 to 6 carbon atoms,
each $R_1$, $R_2$, $R_3$ and $R_4$ is independently hydrogen, phenyl, cycloalkyl of 3 to 5 carbon atoms alkyl of 1 to 5 carbon atoms, or may with adjacent R substitution form an alkylene bridge having 3 or 4 carbon atoms, with the proviso that when there is an alkylene bridge the remaining R substitutions are independently hydrogen, cycloalkyl or alkyl.

2. The process of claim 1 wherein the reaction temperature of the compounds of formulae I and II to III is about 0° C. to about 150° C. and the cyclochlorinating reaction temperature of the compound of formulae III to IV is about 0° C. to about 150° C.

3. The process of claim 1 wherein the reaction temperature of the compounds of formulae I and II to III is about 10° C. to about 120° C. and the cyclochlorinating reaction temperature of the compound of formula III to IV is about 70° C. to about 115° C.

4. The process of claim 1 wherein the compound of formula IV can be prepared with or without isolation of the compound of formula III.

5. The process of claim 1 wherein the reaction temperature of the compounds of formula IV to V is about 0° C. to about 150° C.

6. The process of claim 1 wherein the reaction temperature of the compounds of formula IV to V is about 10° C. to about 120° C.

7. The process of claim 1 wherein the compounds of formula I are 2-amino-4-chlorophenol and 3-amino-5,6,7,8-tetrahydro-2-naphthalenol, formula II is methyl oxalyl chloride and formulae III are 3,6-dichloro-2H-1,4-benzoxazin-2-one and 3-chloro-6,7,8,9-tetrahydronaph[2,3-d]-1,4-oxazine-2-one and the cyclochlorinating agent is phosphorus oxychloride, formula V is 2-ethoxyethyl 5-chloro-2-benzoxazolecarboxylate.

* * * * *